(12) United States Patent
Howarth

(10) Patent No.: US 6,495,698 B1
(45) Date of Patent: Dec. 17, 2002

(54) BINDER-FREE COMPACTED FORMS OF 1,3-DIHALO-5,5-DIMETHYLHYDANTOINS

(75) Inventor: Jonathan N. Howarth, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/484,891

(22) Filed: Jan. 18, 2000

(51) Int. Cl.[7] ................... C07D 233/72; C07D 233/78; C07D 233/86; A01N 59/14; A01N 43/50

(52) U.S. Cl. ................... 548/320.5; 424/405; 424/723; 424/464; 514/388; 510/192; 510/382; 510/381

(58) Field of Search ................... 548/320.5; 424/405, 424/223; 514/388

(56) References Cited

U.S. PATENT DOCUMENTS

| | | | |
|---|---|---|---|
| 2,130,805 A | 9/1938 | Levine | 210/28 |
| 2,392,505 A | 1/1946 | Rogers | 260/309.5 |
| 2,398,598 A | 4/1946 | Rogers | 260/309.5 |
| 2,779,764 A | 1/1957 | Paterson | 260/309.5 |
| 2,795,556 A | 6/1957 | Quinn | 252/187 |
| 2,868,787 A | 1/1959 | Paterson | 260/248 |
| 2,920,997 A | 1/1960 | Wolf et al. | 167/33 |
| 2,971,959 A | 2/1961 | Waugh et al. | 260/309.5 |
| 2,971,960 A | 2/1961 | Waugh et al. | 260/309.5 |
| 3,121,715 A | 2/1964 | Waugh et al. | 260/248 |
| 3,147,219 A * | 9/1964 | Paterson | 252/99 |
| 3,147,259 A | 9/1964 | Paterson | 260/248 |
| 3,345,371 A | 10/1967 | Paterson | 260/192 |
| 3,412,021 A * | 11/1968 | Paterson | 252/99 X |
| 3,626,972 A | 12/1971 | Lorenzen | 137/268 |
| 4,078,099 A | 3/1978 | Mazzola | 427/213 |
| 4,126,717 A | 11/1978 | Mazzola | 427/220 |
| 4,136,052 A | 1/1979 | Mazzola | 252/94 |
| 4,199,001 A | 4/1980 | Kratz | 137/268 |
| 4,242,216 A | 12/1980 | Daugherty et al. | 252/103 |
| 4,270,565 A | 6/1981 | King Sr. | 137/268 |
| 4,293,425 A | 10/1981 | Price | 210/754 |
| 4,327,151 A | 4/1982 | Mazzola | 428/407 |
| 4,331,174 A | 5/1982 | King, Sr. | 137/268 |
| 4,427,692 A | 1/1984 | Girard | 424/237 R |
| 4,465,839 A | 8/1984 | Schulte et al. | 548/310 |
| 4,532,330 A | 7/1985 | Cole | 548/311 |
| 4,537,697 A | 8/1985 | Girard | 252/90 |
| 4,560,766 A | 12/1985 | Girard et al. | 548/311 |
| 4,571,333 A | 2/1986 | Hsiao et al. | 424/22 |
| 4,597,941 A | 7/1986 | Bottom et al. | 422/37 |
| 4,621,096 A | 11/1986 | Cole | 514/389 |
| 4,654,424 A | 3/1987 | Girard et al. | 548/311 |
| 4,659,359 A | 4/1987 | Lorenz et al. | 71/67 |
| 4,662,387 A | 5/1987 | King, Sr. | 137/268 |
| 4,677,130 A | 6/1987 | Puzig | 514/389 |
| 4,698,165 A | 10/1987 | Theyson | 210/755 |
| 4,713,079 A | 12/1987 | Chun et al. | 8/101 |
| 4,728,453 A | 3/1988 | Choy | 252/91 |
| 4,745,189 A | 5/1988 | Lee et al. | 544/221 |
| 4,780,197 A | 10/1988 | Schuman | 210/136 |
| 4,803,079 A | 2/1989 | Hsiao et al. | 424/468 |
| 4,867,895 A | 9/1989 | Choy | 252/91 |
| 4,919,841 A | 4/1990 | Kamel et al. | 252/186.26 |
| 4,925,866 A | 5/1990 | Smith | 514/389 |
| 5,076,315 A | 12/1991 | King | 137/268 |
| 5,218,983 A | 6/1993 | King | 137/1 |
| 5,338,461 A | 8/1994 | Jones | 210/755 |
| 5,339,889 A | 8/1994 | Bigham | 165/1 |
| 5,384,102 A | 1/1995 | Ferguson et al. | 422/264 |
| 5,422,126 A | 6/1995 | Howarth et al. | 424/723 |
| 5,476,116 A | 12/1995 | Price et al. | 137/268 |
| 5,565,109 A | 10/1996 | Sweeny | 210/755 |
| 5,565,576 A | 10/1996 | Hall et al. | 548/317.1 |
| 5,578,559 A | 11/1996 | Dolan et al. | 510/192 |
| 5,591,692 A | 1/1997 | Jones et al. | 504/124 |
| 5,603,941 A | 2/1997 | Farina et al. | 424/405 |
| 5,610,126 A | 3/1997 | Barford et al. | 510/191 |
| 5,614,528 A | 3/1997 | Jones et al. | 514/258 |
| 5,670,451 A | 9/1997 | Jones et al. | 504/134 |
| 5,750,061 A | 5/1998 | Farina et al. | 264/117 |
| 5,753,602 A | 5/1998 | Hung et al. | 510/192 |
| 5,756,440 A | 5/1998 | Watanabe et al. | 510/191 |
| 5,763,376 A | 6/1998 | Ward et al. | 510/191 |
| 5,780,641 A | 7/1998 | Yerushalmi et al. | 548/320.5 |
| 5,859,060 A | 1/1999 | Platt | 514/569 |
| 5,942,153 A | 8/1999 | Heydel | 252/187.33 |
| 5,958,853 A | 9/1999 | Watanabe | 510/192 |
| 5,972,864 A | 10/1999 | Counts | 510/192 |
| 5,981,461 A | 11/1999 | Counts et al. | 510/365 |

FOREIGN PATENT DOCUMENTS

| | | |
|---|---|---|
| CA | 1230825 | 12/1987 |
| CA | 2042430 | 11/1991 |
| CA | 2163596 | 9/1996 |
| EP | 0177645 | 4/1986 |
| EP | 0206725 | 12/1986 |
| EP | 0228593 | 7/1987 |
| EP | 0581826 | 9/1995 |
| GB | 1054243 | 1/1967 |
| GB | 1600289 | 10/1981 |
| GB | 2273106 | 6/1994 |
| WO | 89-10696 | 11/1989 |
| WO | 96-30491 | 10/1996 |
| WO | 97-15652 | 5/1997 |
| WO | 9720546 | 6/1997 |
| WO | 97209009 | 6/1997 |
| WO | 97-43264 | 11/1997 |
| WO | 9743392 | 11/1997 |
| WO | 0034186 | 6/2000 |

OTHER PUBLICATIONS

Corral et al., "Substitution in the Hydantoin Ring. III. Halogenation", J. Org. Chem., 1963, vol. 28, pp. 1100–1104.
Jolles, "General Methods of Bromination", Bromine and its Compounds, 1966, Ernest Benn, London, p. 365.

(List continued on next page.)

Primary Examiner—Joseph K. McKane
(74) Attorney, Agent, or Firm—Edgar E. Spielman, Jr.

(57) ABSTRACT

Novel, binder-free compacted forms of 1,3-dihalo-5,5-dimethylhydantoins in which one halogen atom is chlorine and the other is a bromine or chlorine atom are produced and used for microbiological control in aqueous media and water.

26 Claims, No Drawings

OTHER PUBLICATIONS

Markish et al., "New Aspects on the Preparation of 1,3–Dibromo–5,5–Dimethylhydantoin", Ind. Eng. Chem. Res. 1995, vol. 34, pp. 2125–2127.

Orazi et al., "Halogenacion con 3–Bromo–5,5–Dimetil–Hidantoina", Anales Assoc. Quim. Argentina, 1949, vol. 37, pp. 192–196. (Not translated).

Orazi et al., "Halogenacion Con 1–3–Dibromo–5, 5–Dimetil–Hidantoina", Anales Assoc. Quim. Argentina, 1950, vol. 38, pp. 5–11. (Not translated).

HCAPLUS Abstract of JP 07277912 A2 issued 1995.

HCAPLUS Abstract of JP 08027119 A2 issued 1996.

HCAPLUS Abstract of JP 08239699 A2 issued 1996.

HCAPLUS Abstract of JP 09087684 A2 issued 1997.

HCAPLUS Abstract of JP09227317 A2 issued 1997.

Petterson, "N–Halogen Compounds. I Decomposition of 1,3–Dichloro–5,5–dimethylhydantoin in Water at pH 9", J. Org. Chem., 1959, vol. 24, pp. 1414–1419.

March, "Advanced Organic Chem.", 1992, 4$^{th}$ Edition, pp. 639–640.

HCAPLUS Abstract of JP 07171576 A2 issued 1995.

Krycer et al., "An Evaluation of Tablet Binding Agents Part II. Pressure Binders", Powder Technology, 1983, vol. 34, pp. 53–56.

Chowhan et al., "Hardness Increase Induced by Partial Moisture Loss in Compressed Tablets and Its Effect on In Vitro Dissolution", J. Pharm. Sciences, Oct. 1978, vol. 67, No. 10, pp. 1385–1389.

Author Unknown, "Big Brother Brominator–Brominators", Bulky Systems Website, <Http://www.bulkysystemsinc.com/brominator.html>(visited Aug. 10, 2001,). 1 page.

Author Unknown, "Bio Lab Bromiantor", Conely Company Website, <http://www.conelyco.com/Pool–Spa/parts/biobrom.htm>(visited Aug. 10, 2001). 2 pages.

Hayward America's #1 Pool Water Systems Product Catalog. "Automatic Chemical Feeders" Chlorinators (Slow Dissolve Tri–Chlor Only) and Brominators, Hayward Pool Products Inc. Website, <http://www.haywardnet.com/products/catalog/displayProdInfo.cfm?itemID=61>, 2 pages. Aug. 10,2001.

Hayward Pool Products Owner's Guide, Installation and Operating Instructions, "Hayward Chemical Feeder", Models C250CF, C1100CF, C1800CF, C2400CF,–1998–4 Pages.

Hayward America's 190 1 Pool Water Systems Products Catalog, "Automatic Chemical Feeders" Chlorinators (Slow dissolve Tri–Chlor Only) and Brominators, Buyers Guide, Hayward Pool Products Inc., Website, <http://haywardnet.com/products/catalog/displayProdInfo.cfm?itemID=60<, 2 pages.

Pentair Pool Products Brochure, "Rainbow High Capacity Chlorine/Bromine Feeders", "Unsurpassed Perfornamce From The Industry's Leader in Automatic Sanitizing of Large Residential and commercial Pools", 1 page.

Pentair Pool Products Brochure, "Rainbow Model 300 Automatic Chlorine/Bromine Off–line Feeders", "the Effecient, Easy Way to Sanitize Your Pool of Spa", date Aug. 13, 2001, 1 page.

Pentair Pool Products Brochure, "Rainbow Model 320 Automatic Chlorine/Bromine In–line Feeder", "Saves Time, Reduces Manual Handling of Chemicals", date Aug. 13, 2001, 7 pages.

Sani–King Perform–Max Pool Sanitizer Instruction Guide, Models 910,940, & 980 (Inline) and Models 930 & 960 (off–line), date Aug. 13, 2001, 16 pages.

Sani–King Spa Feeder Product Brochure Model 740 from King Technology Website,<*http://www.kingtechnology.com/spafeeder.htm*>visited (Aug. 10, 2001). 2000, 4 pages.

Sani–King Adjust–A–Flo Product Brochure from King Technology Website<*http://www.kingtechnology.com/spafeeder.htm*>(Visited Aug. 10, 2001), 2000, 1 page.

Sani–King Perform–Max Sanitizers for Inground Pools Product Brochure for Model 940 & 960 from King Technology Website, <http://www.kingtechnology.com/perfermaxIG.htm>, visited Aug. 10, 2001, 2000, 1 page.

Sani–King Perform–Max Sanitizers for Above Ground Pools Product Brochure Model 910 & 930 from King technology Website, <http://www.kingtechnology.com/perfermaxIG.htm>, visited Aug. 10, 2001, 2000, 1 page.

Discount Pool & Spa Supplies, Automatic Chlorinators and Chemical Feeders Website, <*http://www.discountpoolsupplies,com/Chemfeeders/*>visited Aug. 10, 2001, 3 pages.

* cited by examiner

BINDER-FREE COMPACTED FORMS OF 1,3-DIHALO-5,5-DIMETHYLHYDANTOINS

REFERENCE TO OTHER APPLICATIONS

Commonly-owned copending application Ser. No. 09/484,844, filed Jan. 18, 2000, by some of our colleagues, describes and claims chemical processes from which compositions of the present invention can be formed or derived. Commonly-owned copending application Ser. No. 09/484,687, filed Jan. 18, 2000, by some of my colleagues and me, describes and claims 1,3-dibromo-5,5-dimethylhydantoin particulate solids producible by the processes of application Ser. No. 09/484,844, such solids having unprecedented enhanced properties, and compacted articles made from such particulate solids without use of a binder. Commonly-owned copending application Ser. No. 09/487,816, filed Jan. 18, 2000, by one of my colleagues and me, relates in part to converting 1,3-dihalo-5,5-dimethylhydantoins into compacted articles using novel binders. Commonly-owned copending application Ser. No. 09/484,938, filed Jan. 18, 2000, by some of my colleagues and me, describes and claims methods for effecting efficacious microbiological control utilizing 1,3-dibromo-5,5-dimethylhydantoin in novel compacted or non-compacted forms. Commonly-owned copending application Ser. No. 09/483,896, filed Jan. 18, 2000, by one of my colleagues and me, relates to the granulation of small average particle size 1,3-dibromo-5,5-dimethylhydantoin and also to the compaction of such granulated products to form larger-sized articles.

TECHNICAL FIELD

This invention relates to the compacting of 1,3-dihalo-5,5-dimethylhydantoins other than 1,3-dibromo-5,5-dimethylhydantoin without use of binders, and to the novel compacted forms so produced, which, by virtue of their characteristics and physical properties, are superlative biocidal water-treating agents.

GLOSSARY

As used herein the terms "halogen", "halogenated", and "halo" are with reference to bromine or chlorine, or both.

BACKGROUND 1,3-Dihalo-5,5-dialkylhydantoins, especially 1,3-dibromo-5,5-dimethylhydantoin, 1,3-dichloro-5,5-dimethylhydantoin, 1-bromo-3-chloro-5,5-dimethylhydantoin, and 1-chloro-3-bromo-5,5-dimethylhydantoin, or mixtures of two or more of them, are biocidal agents for use in water treatment. These compounds are, in general, sparingly soluble in water. Thus typically they are supplied in solid forms such as granules, tablets, or briquettes, and delivered into the water being treated by means of water flow through an erosion feeder.

Over the years considerable effort has been devoted to the search for improved methods for producing such compounds. In U.S. Pat. No. 2,971,960 N-brominated compounds such as N-brominated 5,5-di-lower-alkyl hydantoins are formed by treating the alkylhydantoin with bromine in an acidic aqueous solution containing hypochlorite, preferably at a pH between 1 and 4. However, the method of choice has been halogenation of the alkylhydantoin in a basic aqueous medium. Almost invariably the halogen has been introduced into, or formed in situ in, the aqueous medium containing the alkylhydantoin. See in this connection U.S. Pat. Nos. 2,398,598; 2,779,764; 2,868,787; 2,920,997; 2,971,959; 3,121,715; 3,147,259; 4,532,330; 4,560,766; 4,654,424; 4,677,130; 4,745,189; PCT Publication No. WO 97/43264, published 20 November 1997; Orazi and Meseri, *Anales Assoc. Quim. Argentina*, 1949, 37, 192–196; Orazi and Meseri, *Anales Assoc. Quim. Argentina*, 1950, 38, 5–11; Corral and Orazi, *J. Org. Chem.*, 1963, 23, 1100–1104; Jolles, *Bromine and its Compounds*, Ernest Benn, London, 1966, p. 365; and Markish and Arrad, *Ind. Eng. Chem. Res.*, 1995, 34, 2125–2127.

The N,N'-dihalogenated dialkylhydantoin products formed by such processes are formed as powdery solids. For use in many applications the dry powders need to be converted into larger forms such as granules, tablets, or briquettes. This in turn has presented problems associated with providing densified or compacted products with sufficient strength to withstand the physical stresses encountered in packaging, conveying, handling, shipping, storage, and use. The nature of these problems have been described, for example, in U.S. Pat. Nos. 4,532,330; 4,560,766; 4,654,424; 4,677,130; 4,745,189; and 5,565,576. The approaches described in these patents for alleviating one or more such problems involve use of additional or other materials. Thus in U.S. Pat. Nos. 4,532,330 and 4,621,096, halogenated dimethylhydantoins are mixed with calcium chloride and water, and the mixture is compacted by compression into the desired shape. In U.S. Pat. Nos. 4,560,766 and 4,654,424, halogenated ethylhydantoins are used instead of halogenated dimethylhydantoins and are compacted as such, or are melt blended with halogenated dimethylhydantoins. U.S. Pat. No. 4,677,130 describes forming dry blends of the halogenated dimethylhydantoin with particulate alkali metal or alkaline earth metal salt followed by compression to form a compacted product such as a tablet. PCT Publication No. WO 97/43264 describes the use of 1,3-bromochloro-5-methyl-5-propyl-hydantoin as a binder in making compacted forms of halogenated hydantoins.

U.S. Pat. No. 4,745,189 describes formation of halogenated dimethylhydantoinby halogenating the hydantoin in an aqueous mixture under alkaline conditions in the presence of a halogenated alicyclic organic compound such as dichloromethane. The Examples of the patent describe the formation of N,N'-bromochloro-5,5-dimethylhydantoin products comprised of large particles.

U.S. Pat. No. 4,560,766 teaches that halogenated dimethylhydantoinper se cannot be used for making low-dust powders, granules, tablets, flakes, compacted forms, cast forms, and carrier-coated products without the aid of a binder.

It would be of great advantage to provide particulate 1,3-dihalo-5,5-dimethylhydantoins useful for making granules, tablets, flakes, compacted forms, cast forms, and carrier-coated products without the aid of a binder, and without use in the production process of any organic halogen compound such as dichloromethane.

SUMMARY OF THE INVENTION

This invention involves the discovery, inter alia, that 1,3-dihalo-5,5-dimethylhydantoins other than 1,3-dibromo-5,5-dimethylhydantoin can be compacted without need of a binder of any kind.

Accordingly, this invention provides, inter alia, novel, binder-free, pressure compacted articles of 1,3-dihalo-5,5-dimethylhydantoins other than 1,3-dibromo-5,5-dimethylhydantoin, and methods of producing such compacted articles from such binder-free 1,3-dihalo-5,5-dimethylhydantoins.

The 1,3-dihalo-5,5-dimethylhydantoins other than 1,3-dibromo-5,5-dimethylhydantoin are 1,3-dichloro-5,5-dimethylhydantoin, 1-bromo-3-chloro-5,5-dimethylhydantoin, and 1-chloro-3-bromo-5,5-dimethylhydantoin, and mixtures thereof. For ease of reference, such compounds (excluding 1,3-dibromo-5,5-dimethylhydantoin) are sometimes referred to hereinafter as "halogenated hydantoins". Even though devoid of a binder, pressure compacted articles formed from particulate halogenated hydantoins have remarkable crush strength. In contrast, so far as is known, all previously known particulate forms of virgin 1,3-dibromo-5,5-dimethylhydantoin cannot be pressure compacted into tablets When attempts were made to form such tablets, it was found that when released from a tableting die, the compacted shape would "delaminate", meaning that the compacted agglomerate would break apart into smaller pieces.

Moreover, when compacted without a binder, granules, tablets, briquettes, or other relatively small shapes formed from the halogenated hydantoins have excellent physical properties for use in water-treatment systems. The shapes erode at slow, but essentially constant, rates when maintained in a constant flow of water. They withstand the customary physical stresses encountered in packaging, conveying, handling, shipping, storage, and use. The compacted solid forms of this invention produced directly from the 1,3-dihalo-5,5-dimethylhydantoins other than 1,3-dibromo-5,5-dimethylhydantoin have excellent crush strength even when formed without a binder.

While many ways of producing halogenated hydantoins are known, the best way of producing them involves process technology fully described in commonly-owned copending application Ser. No. 09/484,844, referred to above.

In converting the halogenated hydantoins into granules, conventional processing equipment can be used under the usual operating conditions. Typically, the finely divided halogenated hydantoin is compressed into sheet form by means of a roll compactor. This sheet in turn is broken up into small granules by a mechanical device, such as a Chilsonator® breaker (The Fitzpatrick Company, Elmhurst, Ill.). The granules are then classified by screening into the desired size range. Undersized granules are typically recycled to the roll compactor, whereas oversized granules are recycled to the breaker device.

The formation of tablets and other compressed shapes such as briquettes from the halogenated hydantoins can also utilize known processing equipment and, for the most part, known procedures. However, in conducting compaction of the virgin halogenated hydantoins particulate solids in the absence of a binder, it is important that the compaction pressure be sufficient to induce plastic deformation and interparticulate binding of the particles. At the same time, the compaction pressure should not be so great as to produce a compacted product which delaminates on expulsion from the die. Typically, suitable compaction pressures in the practice of this invention will fall within the range of about 1000 to about 30,000 psi, and preferably in the range of about 5000 to about 25,000 psi. Such compaction can be conducted using, for example, a rotary tableting press operated at conventional rotational speeds, e.g., about 20 rpm. Another method for accomplishing the compaction is by means of pressure extrusion through a die orifice, while concurrently shearing the extrudate to produce compacted shapes of the desired size. In such operations, the compaction pressures within the die should be sufficient to induce plastic deformation and interparticulate binding of the particles, but insufficient to produce a compacted product which, when extruded, undergoes an elastic recovery of a magnitude that causes delamination of the compacted extrudate.

In operations conducted on a small scale using manually filled dies, 1,3-dichloro-5,5-dimethylhydantoin and N,N'-bromochloro-5,5-dimethylhydantoin having an average particle sizes of about 108 microns and about 324 microns, respectively, have been successfully compacted into tablets without resorting to use of any binder. The tablets when released from the dies were intact and exhibited no visual surface imperfections.

The halogenated hydantoins can also be directly converted without use of a binder into whole briquettes utilizing conventional briquetting rolls operated under conventional conditions. In such operations, pressures in the range of about 1000 to about 30,000 psi are typical; more preferably, the pressures are in the range of from about 5000 to about 25,000 psi. As in the case of pressure compaction of tablets, the compaction pressure should be sufficient to induce plastic deformation and interparticulate binding of the particles, but insufficient to produce a compacted product which undergoes an elastic recovery of a magnitude causing delamination of the compacted article on exiting the rolls.

The compaction operations, whether performed in a die, by extrusion through an orifice of a die, or by roll compaction is typically conducted at ambient room temperatures. However, it is possible to either cool or warm the material being subjected to compaction. This can be accomplished either by refrigerating or directly heating the product before introducing it into the compaction apparatus, or by chilling or heating the apparatus itself such as, for example, by using rolls equipped with heating or cooling coils or other means for effecting temperature regulation. The compaction operation itself can, and in many cases does, result in generation of heat within the compacted shape. Generally speaking, the compaction operations pursuant to this invention can be performed at temperatures in the range of about 5 to about 80° C.

It will be understood and appreciated that departures from the numerical ranges given herein for pressures and temperatures are permissible in the practice of this invention, whenever such departures are deemed necessary or desirable, provided only that such departures do not materially affect in an adverse manner the processing or the properties of the product being produced.

Typically, compacted products of this invention, such as tablets, briquettes, and pucks, formed without use of a binder, will have a crush strength in the range of from about 75 to about 200 pounds per inch of thickness. Thus, it is now possible to provide binder-free compacted products having the strength needed to withstand the physical stresses encountered in packaging, conveying, handling, shipping, storage, and use.

When converted into tablets, briquettes, pucks, and other compacted shapes with use of a suitable binder, the halogenated hydantoins form compacted articles of even greater crush strength. Markedly superior binding agents for use with the halogenated hydantoins are the micronized polyolefins waxes and the micronized polyfluorocarbon waxes described in commonly-owned co-pending application Ser. No. 09/487,816, filed Jan. 18, 2000.

Granules, tablets, and briquettes produced from halogenated hydantoins are of particular utility as biocidal agents for use in swimming pools, spas, toilet bowl cleaners, cooling towers, air washer systems, wastewater, pulp and paper processing operations, oil field applications, and decorative fountains.

In the practice of this invention, the halogenated hydantoin particulate solids used in compaction without a binder are pressure-compactible halogenated hydantoin particulate solids. By this is meant that upon application of pressure to the virgin material in a die, a shape is produced that can be removed from the die without breakage occurring. Experimental evidence to date indicates that 1,3-dichloro-5,5-dimethylhydantoin having an average particle size even as small as about 100 microns or perhaps even less can be successfully pressure compacted into shape-retentive articles. In the case of N,N'-bromochloro-5,5-dimethylhydantoins the available experimental evidence indicates that somewhat larger average particle size product may possibly be required in order to produce shape-retentive articles without use of a binder. The particle size distributions of the halogenated hydantoin may also contribute to the efficacy with which such iparticulate solids can be compacted. Thus in any situation where the pressure compactibility of a given supply of halogenated hydantoin has not been established, it is desirable to perform a preliminary test to determine its suitability in forming a compacted article pursuant to this invention.

Thus, in a preferred group of 1,3-dichloro-5,5-dimethylhydantoin solids in which the average particle size is in the range of about 100 to about 300 microns, 50% of the particles have a particle size of at least about 70 microns.

In a particularly preferred group of 1,3-dichloro-5,5-dimethylhydantoin solids in which the average particle size is in the range of about 100 to about 300 microns, 10 percent of the particles have a particle size of at least about 180 microns, 25 percent of the particles have a particle size of at least about 120 microns, 50 percent of the particles have a particle size of at least about 70 microns, 75 percent of the particles have a particle size of at least about 35 microns, and 90 percent of the particles have a particle size of at least about 20 microns.

In a preferred group of N,N'-bromochloro-5,5-dimethylhydantoin solids in which the average particle size is in the range of about 250 to about 350 microns, 50% of the particles have a particle size of at least about 170 microns.

In a particularly preferred group of N,N'-bromochloro-5,5-dimethylhydantoin solids in which the average particle size is in the range of about 250 to about 350 microns, 10 percent of the particles have a particle size of at least about 800 microns, 25 percent of the particles have a particle size of at least about 400 microns, 50 percent of TA0 the particles have a particle size of at least about 170 microns, 75 percent of the particles have a particle size of at least about 60 microns, and 90 percent of the particles have a particle size of at least about 20 microns.

As also described above, this invention provides products in which one or more of the halogenated hydantoins are converted into granules, tablets, briquettes, pucks, or any other larger sized product, however produced. Typical operations of this type have been described above. Other procedures include, for example, mixing the solid halogenated hydantoin with other dialkylhydantoins and if desired, heat fusing the resultant mixtures, such as described in U.S. Pat. Nos. 4,560,766 and 4,654,424. Similarly, the halogenated hydantoins can be utilized in combination with 1,3-bromochloro-5-methyl-5-propylhydantoin as a binder as described in published PCT Application WO 97/43264.

While there are no hard and fast rules governing differentiation with respect to size among granules, tablets, briquettes, and pucks, typically granules are regarded as being particles ranging in size from about 80 to about 3 U.S. standard mesh size. Tablets typically fall in the range of from about 0.5 to about 1.0 inch in diameter and about 0.5 to about 1.0 inch in thickness. Briquettes will normally range in size from about 0.5 to about 4.0 inches in length, from about 0.5 to about 4.0 inches in width, and from about 0.5 to about 2.5 inches in thickness. Pucks are normally disc-shaped objects having a diameter up to about 3.0 inches and a thickness in the range of about 0.5 to about 1.0 inch. It will be understood and appreciated however, that these dimensions are not intended to unduly limit the scope of this invention.

If desired, the halogenated hydafitoins can be formulated with suitable excipients such as binders, lubricants, disintegrants, and mold release agents. Other optional ingredients which may be used in the formulation of compacted products from these halogenated hydantoins include fragrances, stabilizers, corrosion inhibitors, dyes, other biocidal agents, surfactants, effervescents, diluents, builders, chelating agents, and the like. Such ancillary materials should of course be compatible with the halogenated hydantoin and not interfere in any material way with the performance characteristics of the halogenated hydantoin. The amount(s) of such ancillary materials used should of course be sufficient to serve the purpose for which it is, or they are, being used. At the same time, the amount used should not materially detract from the physical, mechanical, or performance properties of the formulated product.

As indicated above, the halogenated hydantoins can be compacted with or without use of a binder. In the practice of this invention it is preferred to conduct the compaction in the absence of a binder. Commonly-owned co-pending application Ser. No. 09/487,816, filed Jan. 18, 2000, relates in part to the compaction of the halogenated hydantoins using novel binders described therein.

The following Examples are presented to illustrate the practice of, and advantages made possible by, this invention. These Examples are not intended to limit, and should not be construed as limiting, the scope of this invention to the particular operations or conditions described therein.

All particle size determinations referred to in the following Examples were determined by use of a Coulter® LS Particle Size Analyzer. The analyzer was equipped with an LS 230 small volume module and a Fraunhofer PIDS (Polarization Intensity Differential Scattering) detector switched to the "On" position. The determinations were performed at room temperature with a run time of approximately 1 minute per sample. Prior to conducting the particle size determination, and whenever the sample appeared to contain particles adhering to each other, the sample was subjected for 15±1 seconds to sonication using a Sonicor Model SC-100T apparatus to ensure that the particle size measurements were on individual particles of the product, rather than temporarily agglomerated particles.

EXAMPLE 1

Samples of commercially-available N,N'-dihalo-5,5-dimethylhydantoins were obtained and subjected to standard test procedures inorderto determine their average particle size using the Coulter® LS Particle Size Analyzer. Table 1 summarizes the results of these average particle size determinations, and also sets forth the data obtained in the same way on arepresentative sample of the 1,3-dibromo-5,5-dimethylhydantoin product of application Ser. No. 09/484,687. Table 2 summarizes the particle size distribution data on the commercially-available 1,3-dihalo-5,5- dimethylhydantoins. In Table 2 the following abbreviations are used: DCDMH is 1,3-dichloro-5,5-dimethylhydantoin; BCDMH is N,N'-bromochloro-5,5-dimethylhydantoin; and DBDMH is 1,3-dibromo-5,5-dimethylhydantoin.

TABLE 1

| N,N'-dihalo-5,5-dimethylhydantoin | Source | Average Particle Size |
|---|---|---|
| 1,3-dichloro-5,5-dimethylhydantoin | Aldrich Chemical Co. | 108.1 microns |
| N,N'-bromochloro-5,5-dimethylhydantoin | Aldrich Chemical Co. | 323.8 microns |
| 1,3-dibromo-5,5-dimethylhydantoin | Aldrich Chemical Co. | 162.1 microns |
| 1,3-dibromo-5,5-dimethylhydantoin | Albemarle Corporation | 64.5 microns |
| 1,3-dibromo-5,5-dimethylhydantoin | Great Lakes Chemical Corporation | 45.2 microns |
| 1,3-dibromo-5,5-dimethylhydantoin | The product of Application No. 09/484,687 | >500 microns |

TABLE 2

| Particle Size | DCDMH - Aldrich | BCDMH - Aldrich | DBDMH - Aldrich | DBDMH - Albemarle | DBDMH - Great Lakes |
|---|---|---|---|---|---|
| Average | 108.1 $\mu$ | 323.8 $\mu$ | 162.1 $\mu$ | 64.59 $\mu$ | 45.23 $\mu$ |
| 10% is greater than | 195.3 $\mu$ | 877.9 $\mu$ | 359.2 $\mu$ | 162.7 $\mu$ | 78.76 $\mu$ |
| 25% is greater than | 134.4 $\mu$ | 409.9 $\mu$ | 177.6 $\mu$ | 90.12 $\mu$ | 49.76 $\mu$ |
| 50% is greater than | 80.07 $\mu$ | 173.9 $\mu$ | 86.03 $\mu$ | 39.21 $\mu$ | 34.68 $\mu$ |
| 75% is greater than | 45.99 $\mu$ | 65.39 $\mu$ | 47.37 $\mu$ | 26.85 $\mu$ | 23.25 $\mu$ |
| 90% is greater than | 27.19 $\mu$ | 29.35 $\mu$ | 27.67 $\mu$ | 17.91 $\mu$ | 13.90 $\mu$ |
| Range | 0.04–>2000 $\mu$ | 0.04–>2000 $\mu$ | 0.04–>2000 $\mu$ | 0.04–309.6 $\mu$ | 0.04–409.6 $\mu$ |

EXAMPLE 2

The commerically available 1,3-dihalo-5,5-dimethylhydantoins referred to in Example 1 were subjected to tableting operations. Five-gram samples of 1,3-dibromo-5,5-dinethylhydantoin and four-gram samples of DCDMH and BCDMH were compacted without binder in a Sintech® press (MTS Systems Corporation, Edenprairie, Minn.) equipped with a punch and die fabricated from Hastelloy® C alloy. Before manually filling the die, the interior surfaces of the die were lightly dusted with micronized polypropylene wax (MICROPRO 400 wax; Micro Powders, Incorporated, Tarrytown, N.Y.). The pressure applied was 5000 psi with no dwell time, i.e., the pressure was terminated automatically immediately upon reaching 5000 psi. The resultant tablets after removal from the die were aged for 6 days at room temperature. Thereupon the tablets were subjected to crush strength testing utilizing a Sintech® 1/S compression apparatus (MTS Systems Corporation, Edenprairie, Minnesota) equipped with Testworks software, which software is installed in the 1/S compression apparatus as supplied by MTS Systems Corporation. The apparatus includes a horizontal circular-shaped load cell interfaced with a computer, a digital micrometer also interfaced with the computer, and a vertical screw-driven piston that is disposed above the load cell and adapted to apply a downward force perpendicular to the load cell. The procedure for measuring crush strength involves measuring the thickness of the tablet with the micrometer to provide a digitized input to the computer. Next the tablet is placed on its edge on the load cell with the piston in contact with the upper edge of the tablet. Then the apparatus is activated whereby the piston commences applying a progressively increasing downward diametral force to the tablet. At the same time, the load cell continuously measures the downward force being applied to the tablet, and the input of such measurements is transmitted to the computer. When the force being applied reaches the point where the amount of force suddenly decreases to 10% of the immediately preceding force, the tablet has reached the breaking point, and the application of the force is immediately terminated by the software program. From the inputs to the computer, two values are provided, namely the pounds of force at the breaking point of the tablet, and the pounds of force per inch thickness of the tablet at the breaking point. Thus the greater the force applied, the greater the crush strength. The tableting and crush strength tests were conducted using three samples each. It was found that the 1,3-dibromo-5,5-dimethyhydantoin products, obtained from separate commercial sources, could not be tableted. The results of these operations are summarized in Table 3. Each of the crush strength values shown is the average of three tests.

TABLE 3

| Particle Size | DCDMH - Aldrich | BCDMH - Aldrich | DBDMH - Aldrich | DBDMH - Albemarle | DBDMH - Great Lakes |
|---|---|---|---|---|---|
| Average | 108.1 $\mu$ | 323.8 $\mu$ | 162.1 $\mu$ | 64.59 $\mu$ | 45.23 $\mu$ |
| 10% is greater than | 195.3 $\mu$ | 877.9 $\mu$ | 359.2 $\mu$ | 162.7 $\mu$ | 78.76 $\mu$ |
| 25% is greater than | 134.4 $\mu$ | 409.9 $\mu$ | 177.6 $\mu$ | 90.12 $\mu$ | 49.76 $\mu$ |
| 50% is greater than | 80.07 $\mu$ | 173.9 $\mu$ | 86.03 $\mu$ | 39.21 $\mu$ | 34.68 $\mu$ |
| 75% is greater than | 45.99 $\mu$ | 65.39 $\mu$ | 47.37 $\mu$ | 26.85 $\mu$ | 23.25 $\mu$ |
| 90% is greater than | 27.19 $\mu$ | 29.35 $\mu$ | 27.67 $\mu$ | 17.91 $\mu$ | 13.90 $\mu$ |
| Range | 0.04–>2000 $\mu$ | 0.04–>2000 $\mu$ | 0.04–>2000 $\mu$ | 0.04–309.6 $\mu$ | 0.04–409.6 $\mu$ |
| Compaction | Intact tablets | Intact tablets | Delaminated; broken tablets | Delaminated; broken tablets | Delaminated; broken tablets |
| Crush strength lb/in | 183.6 | 83.9 | Test not possible | Test not possible | Test not possible |

As used herein, including the claims, the term "pressure-compactible" means that the substance in particulate form, and without prior treatment to enhance its compactibility, can be converted into a shape-retentive article by application of pressure to the substance when confined in a die, and that such article can be removed from the die without breakage occurring. For example, when the term "pressure-compactible" is applied to a powder or finely-divided material used in forming a tablet, the term means that a shape-retentive tablet is formed when the powder or finely-divided material is subjected to the following conditions:

1) A 0.71 inch diameter circular die fabricated from Hastelloy C alloy is lightly dusted with micronized polypropylene wax (MICROPRO 400 wax; Micro Powders, Incorporated, Tarrytown N.Y., or equivalent if MICROPRO 400 wax is not available).
2) A representative five-gram sample of the given 1,3-dihalo-5,5-dimethylhydantoin other than 1,3-dibromo-5,5-dimethylhydantoin is manually placed into the above die.

3) The five-gram sample is pressure compacted in the die at 5000 psi using a Sintech® press (MTS Systems Corporation, Edenprairie, Minn.) equipped with a punch fabricated from Hastelloy® C alloy to form a 0.71-inch diameter circular tablet. No dwell time is used, i.e., the pressure is released just as soon as the pressure reaches 5000 psi.

4) If no appreciable delamination or breakage occurs when the tablet is released from the die, the given 1,3-dihalo-5,5-dimethylhydantoin other than 1,3-dibromo-5,5-dimethylhydantoin is deemed "pressure-compactible".

As used herein, including the claims, values given for crush strength are as measured using the apparatus and procedure as described in Example 2 above. When the compacted article is in a form other than a cylindrical tablet, the article being tested is to be positioned on the load cell and under the screw-driven piston with the longest axis of the article in the vertical position. In addition, the micrometer is used to measure the thickest portion of the article when the article is positioned on the load cell and under the screw-driven piston with the longest axis of the article in the vertical position.

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions called for pursuant to this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

Each and every patent, publication, or commonly-owned patent application referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A shape-retentive article which comprises a binder-free pressure compacted tablet or puck comprised of at least one pressure-compactible 1,3-dihalo-5,5-dimethylhydantoin in which one of the halogen atoms is a chlorine atom, and the other halogen atom is a bromine or chlorine atom, said hydantoin prior to compaction (i) being devoid of prior treatment to impart compactibility to the solids, and (ii) when said other halogen atom is a chlorine atom, having an average particle size in the range of about 100 to about 300 microns, with 50% of the particles having a particle size of at least about 70 microns, and when said other halogen atom is a bromine atom, having an average particle size in the range of about 250 to about 350 microns, with 50% of the particles having a particle size of at least about 170 microns, said shape-retentive article being comprised of compacted particles of said hydantoin which have undergone compression in a die without undergoing breakage or delamination of the tablet or puck on removal from a die.

2. An article according to claim 1 wherein said article is in the form of granules.

3. An article according to claim 1 wherein said article is in the form of a tablet.

4. An article according to claim 1 wherein said 1,3-dihalo-5,5-dimethylhydantoin is 1,3-dichloro-5,5-dimethylhydantoin.

5. An article according to claim 4 wherein said article is in the form of a tablet having in the diametral direction a crush strength of at least about 25 pounds per inch of thickness.

6. An article according to claim 4 wherein said article is in the form of a tablet having in the diametral direction a crush strength of at least about 50 pounds per inch of thickness.

7. An article according to claim 4 wherein said article is in the form of a tablet having in the diametral direction a crush strength of at least about 100 pounds per inch of thickness.

8. An article according to claim 4 wherein said article is in the form of a tablet having in the diametral direction a crush strength of at least about 150 pounds per inch of thickness.

9. An article according to claim 1 wherein said 1,3-dihalo-5,5-dimethylhydantoin is an N,N'-bromochloro-5,5-dimethylhydantoin.

10. An article according to claim 9 wherein said article is in the form of a tablet having in the diametral direction a crush strength of at least about 25 pounds per inch of thickness.

11. An article according to claim 9 wherein said article is in the form of a tablet having in the diametral direction a crush strength of at least about 50 pounds per inch of thickness.

12. An article according to claim 9 wherein said article is in the form of a tablet having in the diametral direction a crush strength of at least about 75 pounds per inch of thickness.

13. A method of producing a compacted article from a 1,3-dihalo-5,5-dimethylhydantoin, said method comprising pressure compacting in the absence of a binder, a pressure-compactible 1,3-dihalo-5,5-dimethylhydantoin in which one of the halogen atoms is a chlorine atom, and the other halogen atom is a bromine or chlorine atom, said 1,3-dihalo-5,5-dimethylhydantoin being (i) in the form of particulate solids prior to compaction, and (ii) devoid of prior treatment to impart compactibility to said, solids, wherein when said other halogen atom is a chlorine atom, said particulate solids prior to compaction have an average particle size in the range of about 100 to about 300 microns, with 50% of the particles having a particle size of at least about 70 microns, and wherein when said other halogen atom is a bromine atom, said particulate solids prior to compaction have an average particle size in the range of about 250 to about 350 microns, with 50% of the particles having a particle size of at least about 170 microns, the pressure used in the pressure compaction causing particles of said hydantoin to undergo binding in the die without undergoing breakage or delamination on removal of the article from the die.

14. A method according to claim 13 wherein the pressure used to produce said compacted article is in the range of about 5000 psi to about 25,000 psi.

15. A method according to claim 13 wherein the pressure used to produce said compacted article is in the range of from about 1000 psi to about 30,000 psi.

16. A method according to any of claims 13,14, or 15 wherein said hydantoin is 1,3-dichloro-5,5-dimethylhydantoin.

17. A method according to any of claims 13,14, or 15 wherein said hydantoin is N,N'-bromochloro-5,5-dimethylhydantoin.

18. A method which comprises continuously or periodically dispensing from a shape retentive article of claim 1 an amount of a 1,3-dihalo-5,5-dimethylhydantoin in which one of the halogen atoms is a chlorine atom, and the other halogen atom is a bromine or chlorine atom into an aqueous medium or water in an amount effective to effect microbiological control of microbial species present in said aqueous medium or water.

19. A method of claim 18 wherein said 1,3-dihalo-5,5-dimethylhydantoin is dispensed into a sidestream of the aqueous medium or water, and wherein the resultant treated sidestream is brought into contact with a larger body of the aqueous medium or water such that a biocidally effective amount of said 1,3-dihalo-5,5-dimethylhydantoin is delivered to said larger body of aqueous medium or water.

20. A method of claim 18 wherein said 1,3-dihalo-5,5-dimethylhydantoin is dispensed into the aqueous medium or water from a floating device such that a biocidally effective amount of said 1,3-dihalo-5,5-dimethylhydantoin is delivered to the aqueous medium or water.

21. A method of claim 18 wherein the water being treated is recreational water, industrial cooling water, wastewater, or process water.

22. An article according to any of claims 1, 2, 3, 4, 5, 6, 7, 8, 9, 10, 11, or 12 wherein:
  a) prior to compaction and when said other halogen atom is a chlorine atom, 10 percent of the particles of said hydantoin have a particle size of at least about 180 microns, 25 percent of the particles of said hydantoin have a particle size of at least about 120 microns, 50 percent of the particles of said hydantoin have a particle size of at least about 70 microns, 75 percent of the particles of said hydantoin have a particle size of at least about 35 microns, and 90 percent of the particles of said hydantoin have a particle size of at least about 20 microns; and
  b) prior to compaction and when said other halogen atom is a bromine atom, 10 percent of the particles of said hydantoin have a particle size of at least about 800 microns, 25 percent of the particles of said hydantoin have aparticle size of at least about 400 microns, 50 percent of the particles of said hydantoin have a particle size of at least about 170 microns, 75 percent of the particles of said hydantoin have a particle size of at least about 60 microns, and 90 percent of the particles of said hydantoin have a particle size of at least about 20 microns.

23. A method according to any of claims 13, 14, 15, 18, 19, 20, or 21 wherein:
  a) prior to compaction and when said other halogen atom is a chlorine atom, 10 percent of the particles of said hydantoin have a particle size of at least about 180 microns, 25 percent of the particles of said hydantoin have a particle size of at least about 120 microns, 50 percent of the particles of said hydantoin have a particle size of at least about 70 microns, 75 percent of the particles of said hydantoin have a particle size of at least about 35 microns, and 90 percent of the particles of said hydantoin have a particle size of at least about 20 microns; and
  b) prior to compaction and when said other halogen atom is a bromine atom, 10 percent of the particles of said hydantoin have a particle size of at least about 800 microns, 25 percent of the particles of said hydantoin have a particle size of at least about 400 microns, 50 percent of the particles of said hydantoin have a particle size of at least about 170 microns, 75 percent of the particles of said hydantoin have a particle size of at least about 60 microns, and 90 percent of the particles of said hydantoin have a particle size of at least about 20 microns.

24. A method according to claim 23 wherein said other halogen atom is a chlorine atom.

25. A method according to claim 23 wherein said other halogen atom is a bromine atom.

26. A shape-retentive article which comprises a binder-free pressure compacted form of at least one pressure-compactible 1,3-dihalo-5,5-dimethylhydantoin in which one of the halogen atoms is a chlorine atom, and the other halogen atom is a bromine or chlorine atom, said hydantoin prior to compaction being devoid of prior treatment to impart compactibility to the solids, and said article having a crush strength in the range of from about 75 to about 200 pounds per inch of thickness.

* * * * *